United States Patent [19]

Ciaudelli

[11] Patent Number: 4,867,965
[45] Date of Patent: * Sep. 19, 1989

[54] FATTY ACID DIESTERS

[75] Inventor: Joseph P. Ciaudelli, Ramsey, N.J.

[73] Assignee: Revlon, Inc., New York, N.Y.

[*] Notice: The portion of the term of this patent subsequent to Jan. 28, 2003 has been disclaimed.

[21] Appl. No.: 140,932

[22] Filed: Dec. 22, 1987

Related U.S. Application Data

[63] Continuation of Ser. No. 914,423, Oct. 2, 1986, abandoned.

[51] Int. Cl.$^4$ .................. A61K 7/027; A61K 7/42; C07C 69/593; C07C 69/602
[52] U.S. Cl. ................... 424/59; 260/405; 260/410.9 R; 260/410.9 N; 424/64; 424/65; 424/73; 514/785
[58] Field of Search ........ 260/405, 410.9 M, 410.9 R; 514/785; 424/59, 64, 65, 73

[56] References Cited

U.S. PATENT DOCUMENTS

| | | | |
|---|---|---|---|
| 2,163,300 | 6/1939 | Wasson et al. | 260/410.9 Q |
| 2,218,026 | 10/1940 | Hansley | 260/410.9 Q |
| 2,256,353 | 9/1941 | Rheineck et al. | 260/405 |
| 2,397,008 | 3/1946 | Hunter et al. | 260/410.9 Q |
| 2,452,029 | 10/1948 | Bruson et al. | 260/405 |
| 2,500,918 | 3/1950 | Reuter et al. | 260/405 |
| 2,652,411 | 9/1953 | Teeter et al. | 260/405 |
| 3,308,140 | 3/1967 | Roe et al. | 260/405 |
| 3,792,066 | 2/1974 | Rothman et al. | 260/405 |
| 4,567,037 | 1/1986 | Ciaudelli | 424/59 |
| 4,639,369 | 1/1987 | Ciaudelli | 260/405 |
| 4,664,908 | 5/1987 | Woods et al. | 424/59 |

FOREIGN PATENT DOCUMENTS 1952057 10/1969 Fed. Rep. of Germany.
8162553 9/1983 Japan ................... 260/410.9 R

*Primary Examiner*—J. E. Evans

[57] ABSTRACT

Compounds of the formula

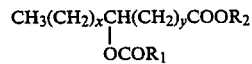

are disclosed wherein $R_1$ is a hydrocarbon radical with 17 carbon atoms and 1–3 double bonds; $R_2$ is a $C_1$–$C_{22}$ hydrocarbon radical, x is 0–4, and y is 0–9.

12 Claims, No Drawings

FATTY ACID DIESTERS

This application is a continuation of prior copending application Ser. No. 914,423, filed Oct. 2, 1986, now abandoned.

BACKGROUND OF THE INVENTION

1. Field of the invention

This invention relates to high molecular weight diesters containing unsaturated hydrocarbon chains.

2. Description of the Prior Art

Organic esters, having the structure $R_1COOR$ wherein $R_1$ and $R$ are identical or different hydrocarbon chains, are widely distributed in nature and may be obtained from animal, vegetable and mineral sources. Such organic esters are in the form of liquid and solid fats, waxes and oils.

All natural fats and oils are mixtures of esters and are distinguished by their melting point range; the oils are liquid at ambient temperature due to the high percentage of unsaturated hydrocarbons in their molecules; the fats are solid or semi-solid. The esters of fats and oils, called triglycerides, are built upon glycerol as the alcohol moiety of the molecule, having the three hydrogens of glycerol replaced with fatty acid radicals. The acids found in fats and oils are straight chain, saturated or unsaturated monocarboxylic acids with four to twenty-six carbon atoms.

Waxes are also mixtures of esters, but differ from fats and oils in that they are monoesters of various alcohols with fatty acids. Most waxes are solids, containing large proportions of saturated fatty acids.

The organic esters are extensively used in cosmetic, household, industrial and pharmaceutical preparations. For example, the lower molecular weight esters are used as solvents in lacquers and nail enamels, perfumery, medicines and artificial flavorings.

While most of the esters can be obtained from natural sources, many lower molecular weight esters and some waxes are also produced synthetically. The synthetically produced esters are utilized analogously to the esters obtained from natural sources and are of great commercial importance.

An object of the present invention is to provide fatty acid esters based on hydroxycarboxylic acids.

Another object of the present invention is to provide fatty acid esters for use in cosmetic compositions.

SUMMARY OF THE INVENTION

These and other objects are achieved by a diester obtained by: first esterifying a hydroxy acid with a long chain unsaturated fatty acid to form an unsaturated esterified acid; then, reacting the unsaturated esterified acid with an alcohol to produce a diester of the present invention.

The fatty acid diesters of the present invention have the general formula $$CH_3(CH_2)_x CH(OCOR_1)(CH_2)_y COOR_2$$

wherein $R_1$ is a hydrocarbon radical having 17 carbon atoms with 1 to 3 double bonds;

$R_2$ is a straight or branched-chain hydrocarbon radical having 1 to 22 carbon atoms;

$x$ is 0–4; and $y$ is 0–9

Examples of fatty acid diesters of the present invention include:
Methyl Oleoyl Oxyvalerate
Ethyl Oleoyl Oxyvalerate
Isopropyl Oleoyl Oxyvalerate
Butyl Oleoyl Oxyvalerate
Isobutyl Oleoyl Oxyvalerate
Octyl Oleoyl Oxyvalerate
Ethylhexyl Oleoyl Oxyvalerate
Isocetyl Oleoyl Oxyvalerate
Isodecyl Oleoyl Oxyvalerate
Octyldodecyl Oleoyl Oxyvalerate
Isostearyl Oleoyl Oxyvalerate
Amyl Oleoyl Oxyvalerate Also included are compounds corresponding to the above in which (A) the oleoyl radical is instead linoleoyl or linolenoyl, or (B) the oxyvalerate is instead oxycaproate, oxybutyrate, lactate, and the like, or (C) both (A) and (B) are present.

The diesters of the present invention and synthesis thereof will be illustrated by the examples that follow:

EXAMPLE 1

Isopropyl Oleoyl Oxyvalerate (A) 180 grams of hydroxyvaleric acid, 425 grams of oleic acid (Emery - Emersol 233LL) and 4 grams of dibutyl tin oxide (Aldrich Chem. Co.) are mixed and heated to 190° C. in a 2-liter, 3-neck flask until the esterification reaction is completed. Water forming during this esterification reaction is collected in a Dean-Stark trap. (B) The oleoyl oxyvaleric acid obtained in A above is mixed with isopropanol. The mixture is heated and the water formed by the reaction is collected by a Dean-Stark trap. The reaction product, isopropyl oleoyl oxyvalerate, is treated with charcoal and filtered through a Buchner funnel.

It is to be noted, that the temperature used during the reaction may be lowered, and the reaction time may be shortened, by using a nitrogen sparge to drive water over during the esterification reaction.

EXAMPLE 2

Octyldodecyl Linoleoyl Oxyvalerate

The preparation of the title compound is analogous to the preparation in Example 1, except that, instead of oleic acid, linoleic acid (Emery's Emersol 315) is used, and octyldodecyl alcohol is used instead of isopropanol.

EXAMPLE 3

Butyl Linoleoyl Oxybutyrate

The title compound is prepared using linoleoyl oxybutyric acid and butyl alcohol according to the procedure described in Example 1.

The compounds of the present invention may be easily formulated into cosmetic compositions, household and pharmaceutical products.

In general, a cosmetic formulation for skin care comprises the following ingredients by weight:

1–20% of the diester of the present invention or mixtures thereof;

5–10% of a humectant, such as glycerin, propylene glycol, sorbitol and mineral oil;

0.2–1.0% of a thickener, such as carboxyvinyl polymers, methyl cellulose, hydroxymethyl cellulose and hydroxypropyl cellulose;

0.5–10% of an emulsifier, such as sorbitan stearate, sorbitan palmitate, glyceryl stearate and glycol stearate; and 50–80% water.

In addition other ingredients conventionally used in cosmetic preparations may be used, such as preservatives, coloring agents and perfumes.

Examples 4, 5, 6 and 7 illustrate cosmetic compositions which can be made embodying the present invention.

EXAMPLE 4

Cosmetic Cream

|  | % w/w |
| --- | --- |
| Octyldodecyl Oleoyl Oxyvalerate | 8.00 |
| Mineral Oil | 10.00 |
| Glycerol Monostearate | 10.00 |
| Methyl Paraben | 0.10 |
| Propyl Paraben | 0.15 |
| Perfume | 0.25 |
| Water | 71.50 |

EXAMPLE 5

Cosmetic Cream

|  | % w/w |
| --- | --- |
| Water | 61.25 |
| Carbopol 934 Solution | 5.00 |
| Isopropyl Oleoyl Oxyvalerate | 8.00 |
| Propylene Glycol | 7.00 |
| Methyl Paraben | 0.30 |
| Propyl Paraben | 0.10 |
| Glyceryl Stearate | 4.00 |
| Cetyl Alcohol | 1.20 |
| Stearic Acid | 2.40 |
| Mineral Oil | 8.00 |
| Steareth 20 | 1.00 |
| Triethanolamine | 1.40 |
| Trisodium EDTA | 0.05 |
| Quaternium 15 | 0.10 |
| Dimethicone | 0.20 |

EXAMPLE 6

Another formulation which provides a thicker hand cream than Example 5 is as follows:

|  | % w/w |
| --- | --- |
| Butyl Linoleoyl Oxybutyrate | 8.00 |
| Cetyl Alcohol | 1.00 |
| Mineral Oil | 10.00 |
| Glyceryl Monostearate | 10.00 |
| Methyl Paraben | 0.10 |
| Propyl Paraben | 0.15 |
| Perfume | 0.25 |
| Water | 70.50 |

EXAMPLE 7

This example illustrates the compatibility of the diesters with other cosmetic ingredients: the formula contains both a suntanning agent and a sunscreening agent.

|  | % w/w |
| --- | --- |
| Amyl Linoleoyl Oxycaproate | 4.00 |
| Mineral Oil | 8.00 |
| Glyceryl Monostearate SE | 8.00 |
| Cetyl Alcohol | 0.50 |
| Parsol MCX* | 5.00 |
| Propyl Paraben | 0.10 |
| Methyl Paraben | 0.15 |
| Unipertan P-24** | 5.00 |
| Perfume | 0.25 |
| Water | 69.00 |

*Tradename for Givaudan's 2-Ethylhexyl-p-methoxycinnamate
**Tradename for Induchem's Tyrosine complex.

Regarding cosmetic compositions, there may be mentioned in particular, those which are presented in the form of fluid emulsions, lotions, creams and lipstick bases. For example, the cosmetic compositions may be emollient milks or creans for face and hand care, make-up foundations, sunscreen milks or creams, antiperspirant milks or creams and shaving creams.

While various preferred embodiments of the present invention have been illustrated by means of specific examples, it is to be understood that the present invention is in no way to be deemed as limited thereto, but should be construed as broadly as defined by the appended claims.

What is claimed is:

1. A diester of the formula $$CH_3(CH_2)_x CH(OCOR_1) (CH_2)_y COOR_2$$

wherein, $R_1$ is a hydrocarbon radical having 17 carbon atoms with 1 to 3 double bonds therein;

$R_2$ is a hydrocarbon radical having 1 to 22 carbon atoms;

x is 0–4; and y is 0–9.

2. The diester of claim 1 wherein $R_1$ is oleyl.

3. The diester of claim 1 wherein $R_1$ is linoleyl.

4. The diester of claim 1 wherein $R_1$ is linolenyl.

5. The diester of claim 2 wherein $R_2$ is ethyl, isopropyl, butyl, or isobutyl.

6. The diester of claim 3 wherein $R_2$ is ethyl, isopropyl, butyl, or isobutyl.

7. The diester of claim 4 wherein $R_2$ is ethyl, isopropyl, butyl or isobutyl.

8. The diester of claim 2 wherein $R_2$ contains 5 to 22 carbon atoms.

9. The diester of claim 3 wherein $R_2$ contains 5 to 22 carbon atoms.

10. The diester of claim 4 wherein $R_2$ contains 5 to 22 carbon atoms.

11. A cosmetic composition comprising by weight 1–20% of a diester according to claim 1.

12. A cosmetic composition according to claim 11 further comprising by weight:
5–10% of a humectant;
0.2–1.0% of a thickener;
0.5–10% of an emulsifier; and
50–80% water.

* * * * *